United States Patent
Elder et al.

(10) Patent No.: US 9,470,649 B2
(45) Date of Patent: Oct. 18, 2016

(54) HAND-HELD TEST MESTER WITH LOW-DISTORTION SIGNAL GENERATION CIRCUIT

(71) Applicant: LifeScan Scotland Limited, Inverness (GB)

(72) Inventors: David Elder, Inverness (GB); Rossano Massari, Milan (IT)

(73) Assignee: LifeScan Scotland Limited, Inverness (GB)

( * ) Notice: Subject to any disclaimer, the term of this patent is extended or adjusted under 35 U.S.C. 154(b) by 259 days.

(21) Appl. No.: 14/300,454

(22) Filed: Jun. 10, 2014

(65) Prior Publication Data

US 2015/0355131 A1  Dec. 10, 2015

(51) Int. Cl.
 *G01R 23/20* (2006.01)
 *G01N 27/26* (2006.01)
 (Continued)

(52) U.S. Cl.
 CPC ...... *G01N 27/3273* (2013.01); *G01N 27/3271* (2013.01); *G01N 27/3274* (2013.01); *G01R 23/20* (2013.01); *G01N 29/26* (2013.01)

(58) Field of Classification Search
 CPC ........... G01N 27/327; G01N 27/3271; G01N 27/3273; G01N 27/3274; G01N 33/487; G01N 33/48785; G01N 33/66; G01N 23/20; G01N 29/26; G01N 31/31708; H03B 28/00; H03K 3/80
 USPC ................ 324/620, 612, 600; 205/775, 792; 435/4, 14
 See application file for complete search history.

(56) References Cited

U.S. PATENT DOCUMENTS 3,491,282 A    1/1970  Heinrich et al.
5,465,203 A *  11/1995 Bhattacharya ............ H02J 3/01
                                                    307/105

(Continued)

FOREIGN PATENT DOCUMENTS

CN      101478286 A    7/2009
EP        1775587 A2   4/2007

(Continued)

OTHER PUBLICATIONS

International Search Report and Written Opinion issued in corresponding International Patent Application No. PCT/EP2015/062839, date mailed Oct. 2, 2015, 11 pages.

(Continued)

*Primary Examiner* — Hoai-An D Nguyen

(57) ABSTRACT

A hand-held test meter for use with an analytical test strip in the determination of an analyte in a bodily fluid sample includes a housing, a clock module disposed in the housing, a micro-controller disposed in the housing, a low-distortion signal generation circuit block ("LDSGCB") disposed in the housing, and a strip port connector configured to operationally receive the analytical test strip. The LDSGCB includes a signal summation circuit ("SSC") sub-block, a resistance-capacitance (RC) filter, and a single operational amplifier. The clock module and micro-controller are configured to generate phase-shifted square wave signals and output the phase-shifted square wave signals to the SSC. The SSC is configured to sum the phase-shifted square wave signals to generate a resultant summed-wave signal and output the resultant summed-wave signal to the RC filter. The RC filter is configured to filter harmonics from the resultant summed-wave signal thereby creating a reduced harmonic distortion signal.

27 Claims, 8 Drawing Sheets

(51) Int. Cl.
*G01N 27/327* (2006.01)
*G01R 29/26* (2006.01)

(56) References Cited

U.S. PATENT DOCUMENTS

| | | | | |
|---|---|---|---|---|
| 5,640,960 A | * | 6/1997 | Jones | A61B 8/0866 |
| | | | | 600/453 |
| 2007/0084734 A1 | | 4/2007 | Roberts et al. | |
| 2007/0087397 A1 | | 4/2007 | Kraft et al. | |
| 2008/0087544 A1 | * | 4/2008 | Zhou | G01N 27/48 |
| | | | | 204/406 |
| 2011/0315564 A1 | | 12/2011 | Guthrie et al. | |
| 2013/0084589 A1 | | 4/2013 | Kraft et al. | |
| 2013/0084590 A1 | * | 4/2013 | Lugo Jimenez | G01N 27/3274 |
| | | | | 435/14 |
| 2013/0217053 A1 | * | 8/2013 | Mackintosh | G01N 27/3274 |
| | | | | 435/14 |
| 2014/0202882 A1 | * | 7/2014 | McIlrath | G01N 27/3274 |
| | | | | 205/782 |
| 2014/0326614 A1 | * | 11/2014 | Guthrie | G01N 27/307 |
| | | | | 205/775 |
| 2015/0073718 A1 | * | 3/2015 | Elder | G01N 33/49 |
| | | | | 702/19 |

FOREIGN PATENT DOCUMENTS

| | | |
|---|---|---|
| EP | 2020600 A2 | 4/2009 |
| GB | 1300807 | 12/1972 |
| JP | H02239705 A | 9/1990 |
| WO | 2010/049669 A1 | 5/2010 |
| WO | 2012/001351 A1 | 1/2012 |
| WO | 2012/042211 A2 | 4/2012 |
| WO | 2012/164271 A1 | 12/2012 |

OTHER PUBLICATIONS

Combined Search Report and Examination Report issued in Application No. GB 1223262.5, dated Mar. 19, 2013, 7 pages.

* cited by examiner

HAND-HELD TEST MESTER WITH LOW-DISTORTION SIGNAL GENERATION CIRCUIT

BACKGROUND OF THE INVENTION

1. Field of the Invention

The present invention relates, in general, to medical devices and, in particular, to test meters and related methods.

2. Description of Related Art

The determination (e.g., detection and/or concentration measurement) of an analyte in, or characteristic of, a bodily fluid sample is of particular interest in the medical field. For example, it can be desirable to determine glucose, ketone bodies, cholesterol, lipoproteins, triglycerides, acetaminophen, hematocrit and/or HbA1c concentrations in a sample of a bodily fluid such as urine, blood, plasma or interstitial fluid. Such determinations can be achieved using a hand-held test meter in combination with analytical test strips (e.g., electrochemical-based analytical test strips).

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings, in which like numerals indicate like elements, of which:

DETAILED DESCRIPTION OF ILLUSTRATIVE EMBODIMENTS

Figure 1:
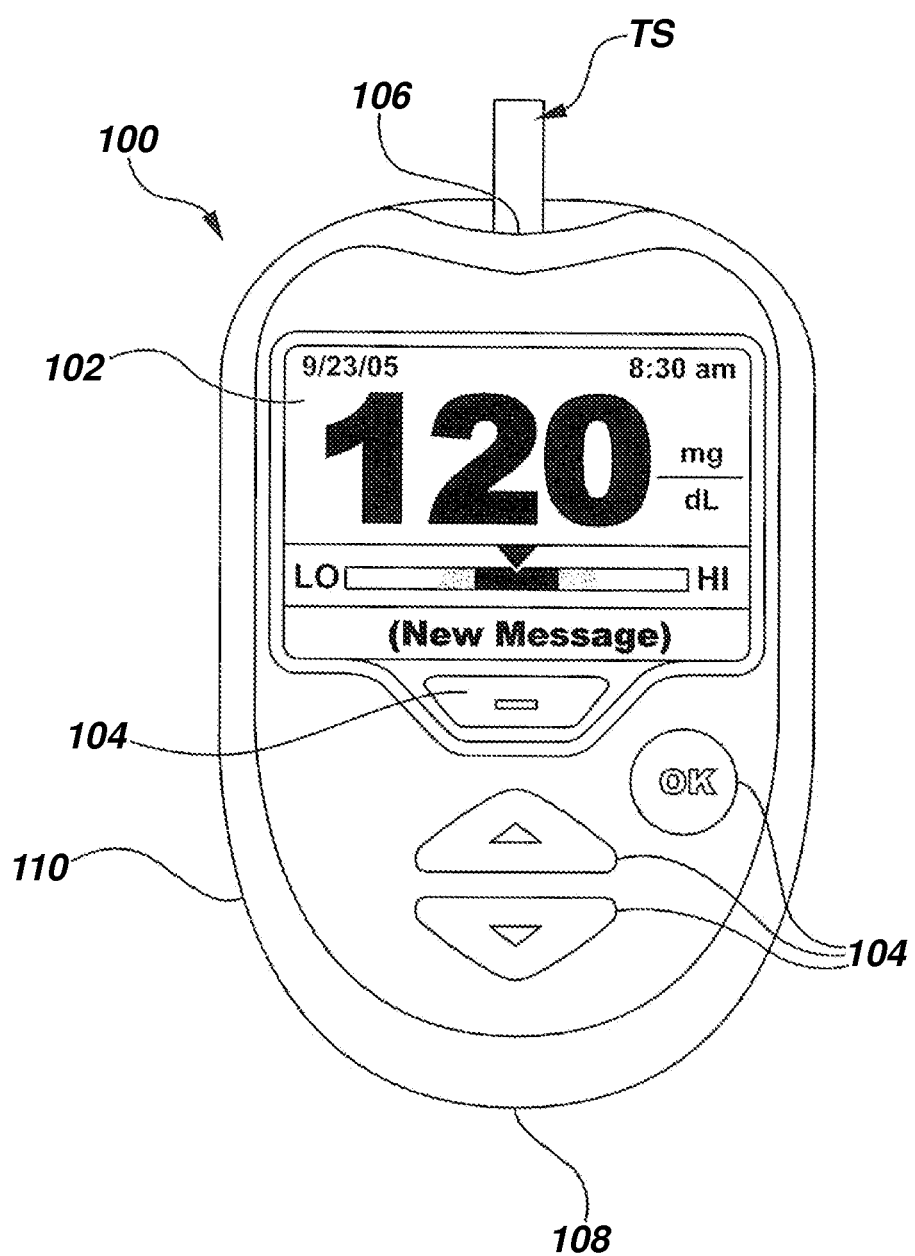
FIG. 1 is a simplified depiction of a hand-held test meter according to an embodiment of the present invention.

The following detailed description should be read with reference to the drawings, in which like elements in different drawings are identically numbered. The drawings, which are not necessarily to scale, depict exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein.

In general, hand-held test meters for use with an analytical test strip in the determination of an analyte in, and/or a characteristic of, a bodily fluid sample according to embodiments of the present invention include a housing, a clock module disposed in the housing, a micro-controller disposed in the housing, a low-distortion signal generation circuit block disposed in the housing, and a strip port connector configured to operationally receive an analytical test strip. The low-distortion signal generation circuit block includes a signal summation circuit sub-block, a resistance-capacitance (RC) filter, and a single operational amplifier.

The clock module and micro-controller are configured to generate a plurality of phase-shifted square wave signals and output the plurality of phase-shifted square wave signals to the signal summation circuit. The signal summation circuit is configured to sum the phase-shifted square wave signals to generate a resultant summed-wave signal and output the resultant summed-wave signal to the RC filter. Furthermore, the RC filter is configured to filter harmonics from the resultant summed-wave signal, thereby creating a reduced harmonic distortion signal. The single operational amplifier is configured to amplify the reduced harmonic distortion signal to produce an amplified reduced harmonic distortion signal that is output to an analytical test strip received in the strip port connector.

Hand-held test meters according to embodiments of the present invention are beneficial in that they provide improved accuracy of determination using an inexpensive low-distortion signal generation circuit block. In addition, since the low-distortion signal generation circuit block includes only a single operational amplifier, it requires relatively little space in the hand-held test meter housing. The low-distortion signal generation circuit block is low cost since, for example, it includes only a single active component, namely the single operational amplifier with the remainder of the circuit being composed of passive components such as batteries (or other suitable power rail source), resistors and capacitors. Despite including only a single operational amplifier, the low-distortion signal generation circuit block generates a reduced harmonic distortion signal that is beneficially low in distortion (e.g., having a Total Harmonic Distortion (THC) of less than, for example, 1.1% and 0.8% for $2^{nd}$ and $4^{th}$ order harmonics respectively) and, therefore, particularly suitable for the use in high accuracy determinations.

Once one skilled in the art is apprised of the present disclosure, he or she will recognize that an example of a hand-held test meter that can be readily modified as a hand-hand test meter according to the present invention is the commercially available OneTouch® Ultra® 2 glucose meter from LifeScan Inc. (Milpitas, Calif.). Additional examples of hand-held test meters that can also be modified are found in U.S. Patent Application Publications Nos. 2007/0084734 (published on Apr. 19, 2007) and 2007/0087397 (published on Apr. 19, 2007) and in International Publication Number WO2010/049669 (published on May 6, 2010), each of which is hereby incorporated herein in full by reference. In addition, the use other circuit configurations for the determination of hematocrit is described in U.S. patent application Ser. No. 13/008,405, which is also hereby incorporated in full by reference.

Figure 2:
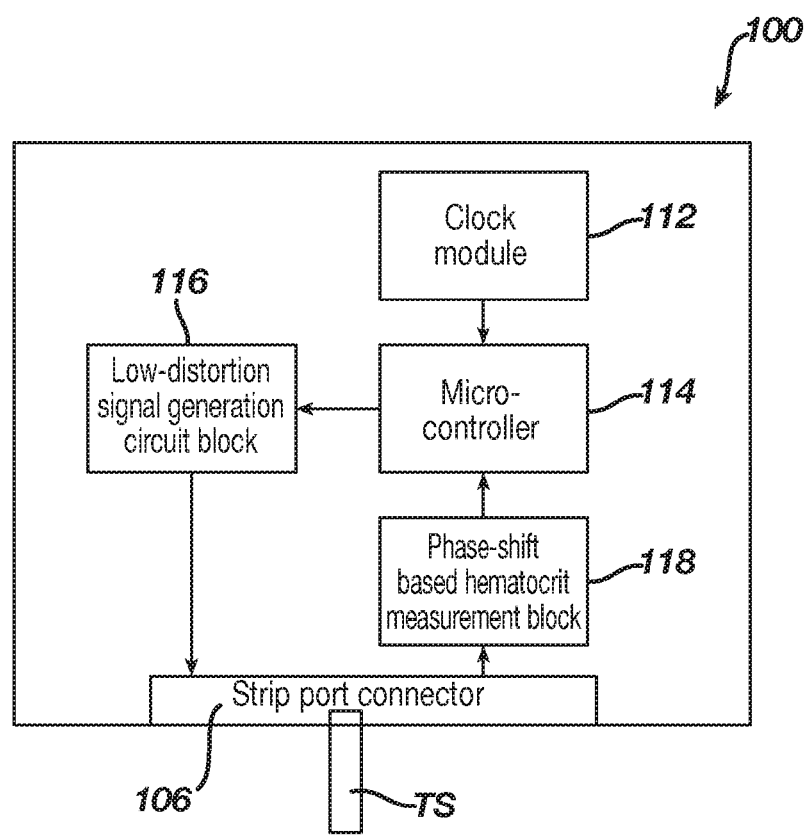
FIG. 2 is a simplified block diagram of various blocks of the hand-held test meter of FIG. 1.
Figure 3:
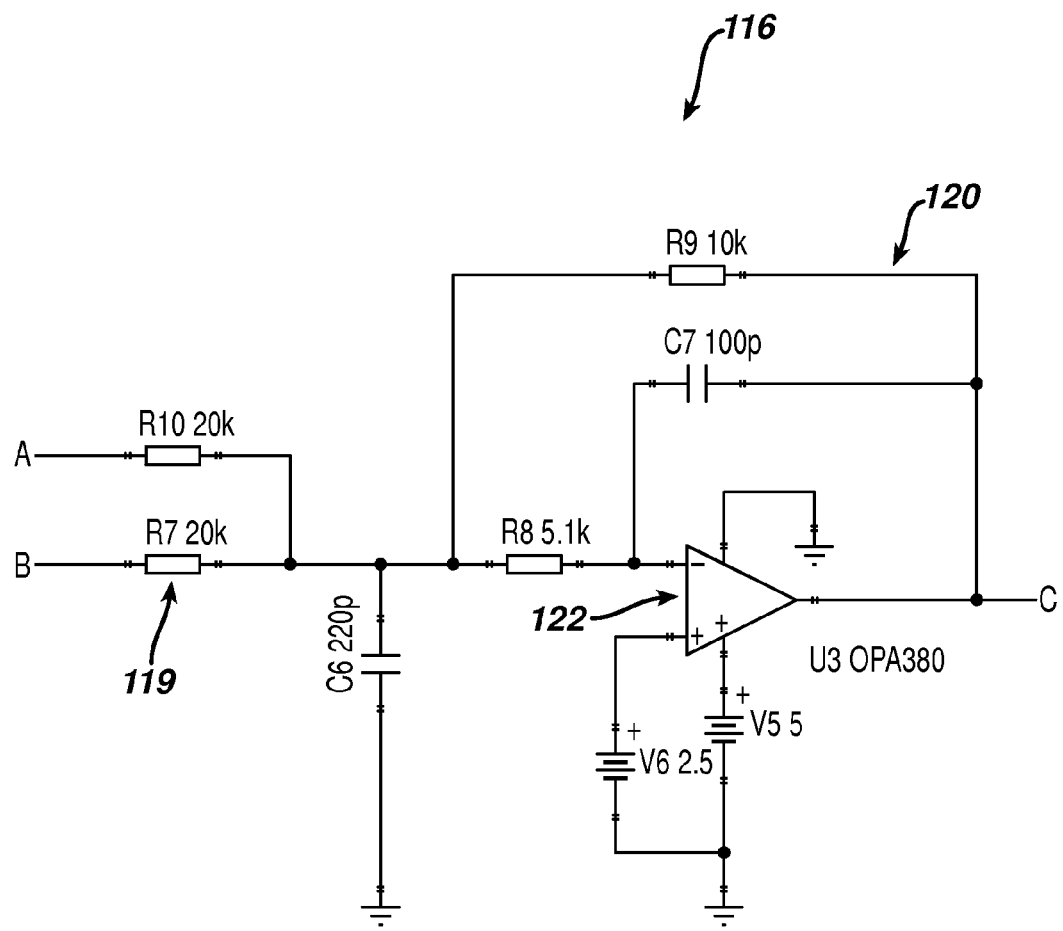
FIG. 3 is a simplified schematic diagram of a low-distortion signal generation circuit block as can be employed in embodiments of the present invention.
Figure 4:
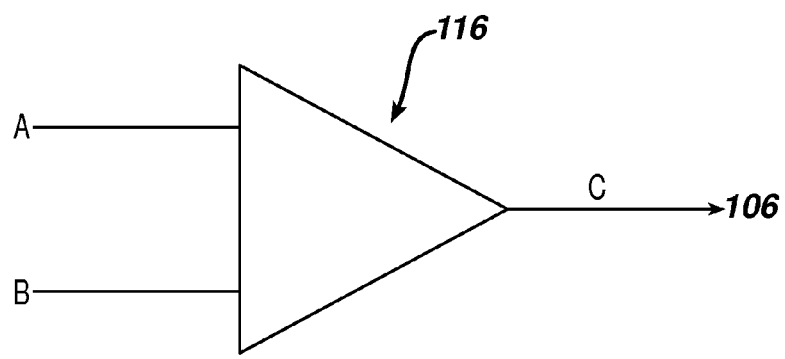
FIG. 4 is a more simplified (i.e., reduced to one active component) schematic of the low distortion signal generation circuit block of FIG. 3.
Figure 5:
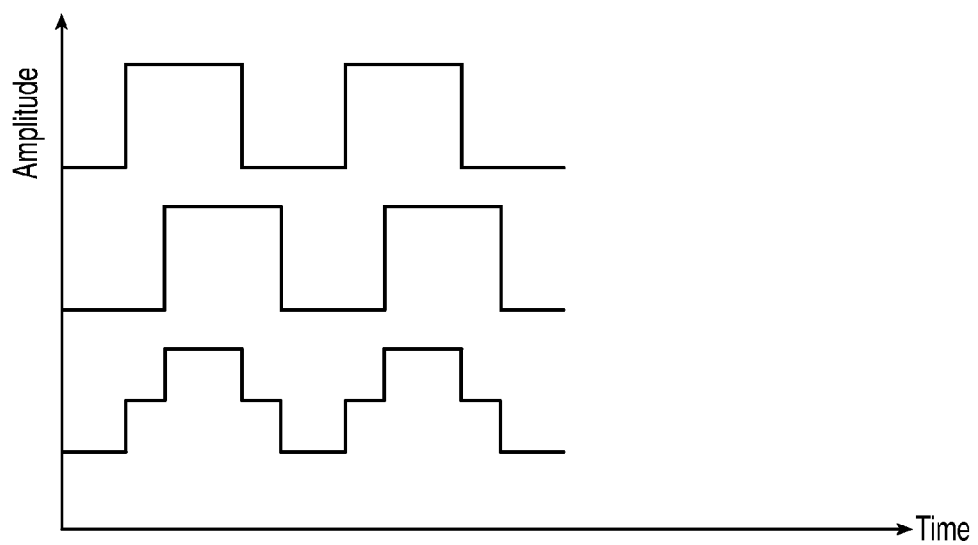
FIG. 5 is a simplified stacked depiction of two phase-shifted square wave signals and a resultant summed-wave signal that employs a stacked y-axis format.

FIG. 1 is a simplified depiction of a hand-held test meter 100 for the determination of an analyte in a bodily fluid sample according to an embodiment of the present invention. FIG. 2 is a simplified block diagram of various blocks of hand-held test meter 100. FIG. 3 is a simplified schematic diagram of a low-distortion signal generation circuit block as can be employed in embodiments of the present invention including hand-held test meter 100. FIG. 4 is a more simplified (i.e., reduced to one active component) schematic of the low distortion signal generation circuit block of FIG. 3. FIG. 5 is a simplified stacked depiction of two phase-shifted square wave signals and a resultant summed-wave signal.

Figure 6:
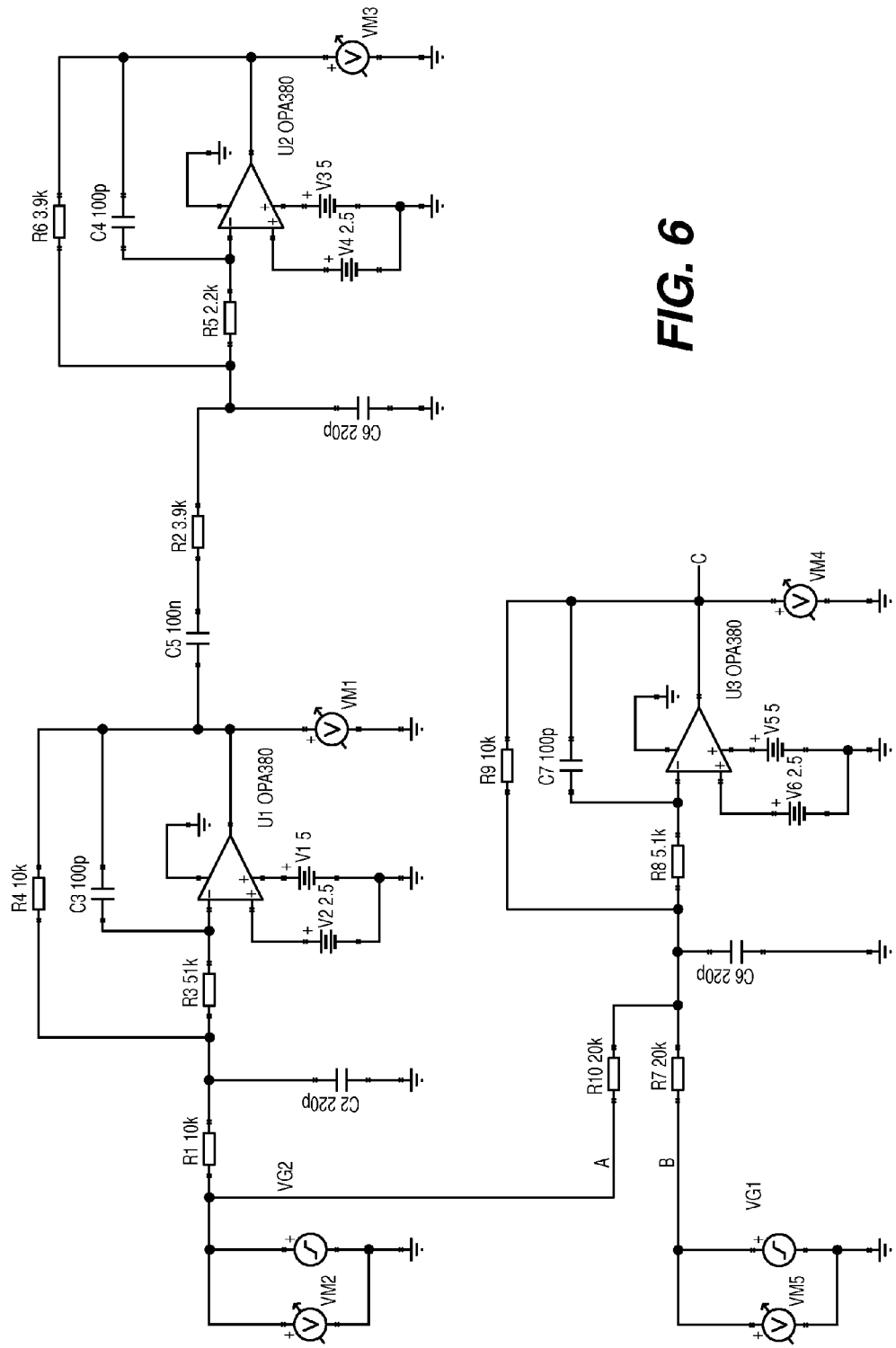
FIG. 6 is a simplified electrical schematic of an electrical circuit block used for various simulations, including a simulation of (i) a low-distortion signal generation circuit block as can be employed in various embodiments of the present invention and (ii) an alternative signal generation circuit block.
Figure 7:
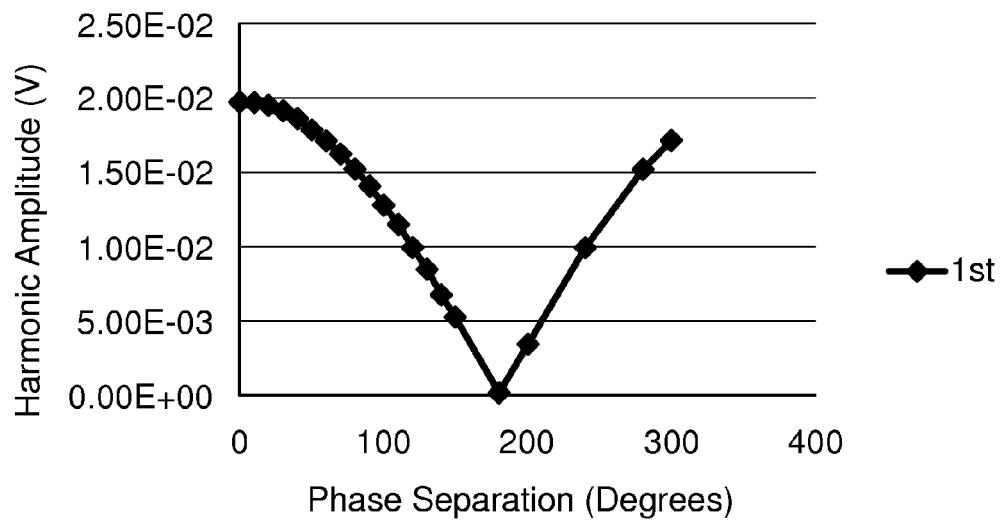
FIG. 7 is a simplified graph of a $1^{st}$ harmonic simulation amplitude results versus phase separation generated using the electrical circuit block of FIG. 6.
Figure 8:
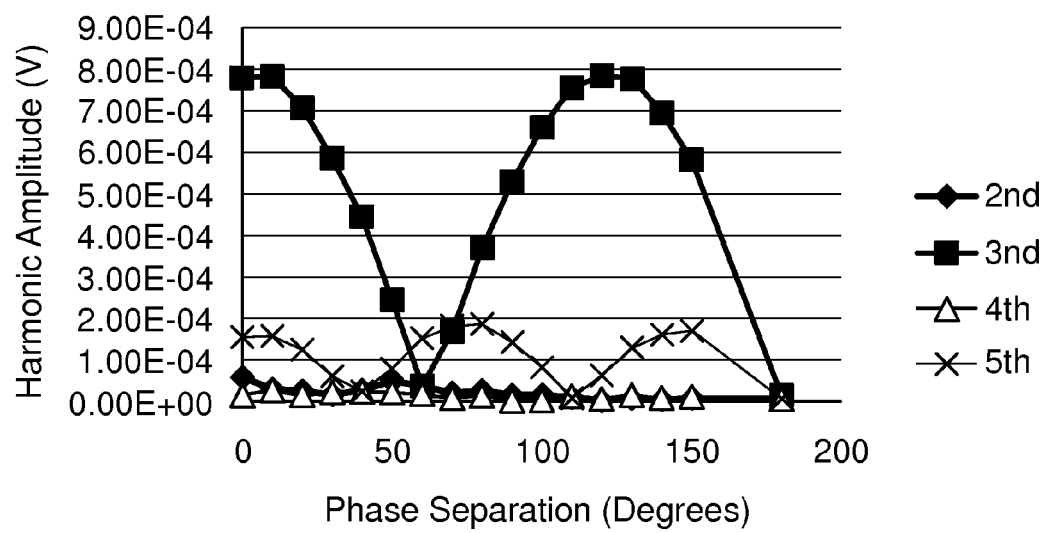
FIG. 8 is a simplified graph of $2^{nd}$, $3^{rd}$, $4^{th}$ and $5^{th}$ harmonic simulation amplitude results versus phase separation generated using the electrical circuit block of FIG. 6.
Figure 9:
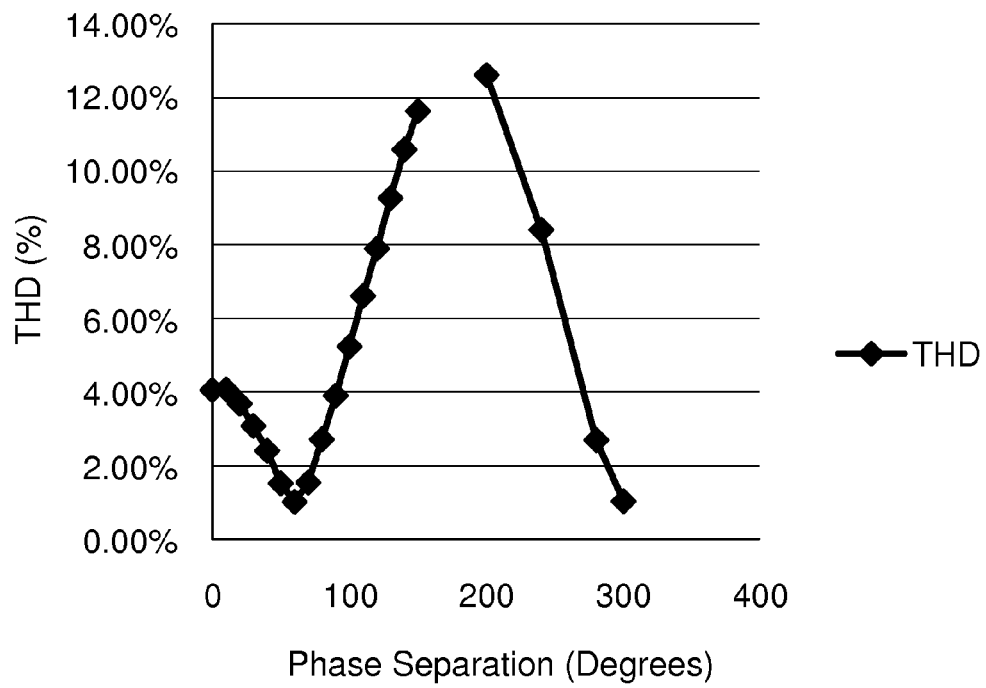
FIG. 9 is a simplified graph of Total Harmonic Distortion (THD) results versus phase separation generated using the electrical circuit block of FIG. 6.
Figure 10:
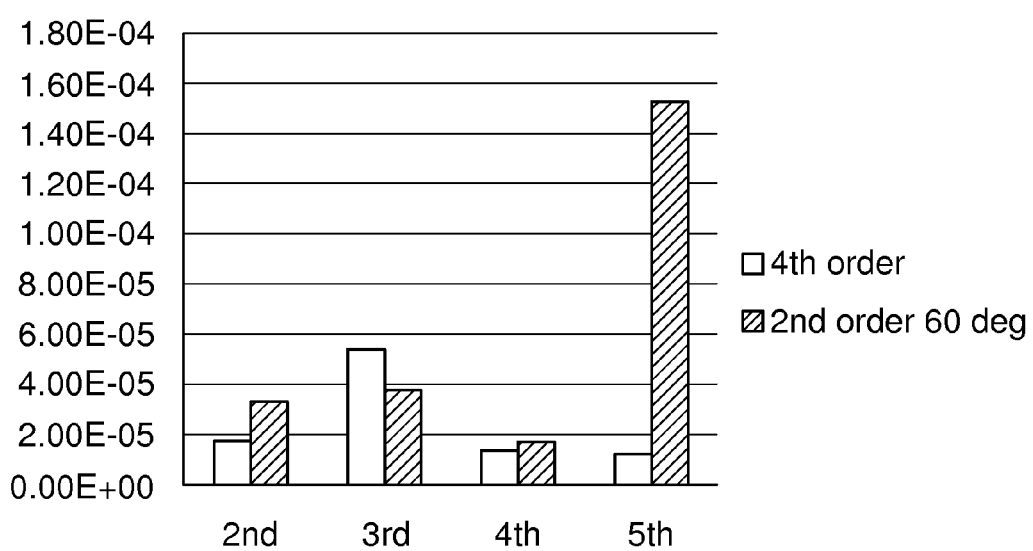
FIG. 10 is a bar chart (with the y-axis representing relative strength) comparing harmonic simulation amplitude results for a low-distortion signal generation block employing $2^{nd}$ order filtration and +/−60-degree square wave phase separation as can be employed in embodiments of the present invention and an alternative signal generation block employing a $4^{th}$ order filter.

FIG. 6 is a simplified electrical schematic of an electrical circuit block 200 used for various simulations, including (i) a simulation of a low-distortion signal generation circuit block as can be employed in various embodiments of the present invention and (ii) an alternative signal generation circuit block. FIG. 7 is a simplified graph of a $1^{st}$ harmonic simulation amplitude results versus phase separation generated using electrical circuit block 200. FIG. 8 is a simplified graph of $2^{nd}$, $3^{rd}$, $4^{th}$ and $5^{th}$ harmonic simulation amplitude results versus phase separation generated using electrical circuit block 200. FIG. 9 is a simplified graph of Total Harmonic Distortion (THD) versus phase separation generated using electrical circuit block 200. FIG. 10 is a bar chart comparing harmonic simulation amplitude results for a low-distortion signal generation block employing $2^{nd}$ order filtration and ±60-degree square wave phase separation as can be employed in embodiments of the present invention and an alternative signal generation block employing a $4^{th}$ order filter.

In FIGS. 3, 4 and 6, "A" represents a first phase-shifted square wave signal, "B" represents a second phase-shifted square wave signal, and "C" represents an amplified reduced harmonic distortion signal (for example, an amplified reduced harmonic distortion sine wave signal) that is output to an analytical test strip received in the strip port connector. Signal "A" can be, for example, a 250 kHz digital square wave at 1V peak-to-peak and phase-shifted by +30 degrees. Signal "B" can be, for example, a 250 kHz digital square wave at 1V peak-to-peak and phase-shifted by −30 degrees. Signal "C" can be, for example, a 250 KHz digital sine wave at 10 mV peak-to-peak.

Referring to FIGS. 1 through 10, hand-held test meter 100 includes a display 102, a plurality of user interface buttons 104, a strip port connector 106, a USB interface 108, and a housing 110 (see FIG. 1). Referring to FIG. 2 in particular, hand-held test meter 100 also includes a clock module 112, a micro-controller 114, a low-distortion signal generation circuit block 116, a phase-shift-based hematocrit measurement block 118 and other electronic components (not shown) for applying a test voltage to analytical test strip (labeled TS in FIGS. 1 and 2), and also for measuring an electrochemical response (e.g., plurality of test current values) and determining an analyte or characteristic based on the electrochemical response. To simplify the current descriptions, the figures do not depict all such electronic circuitry.

Low-distortion signal generation circuit block 116 includes a signal summation circuit sub-block 119; a resistance-capacitance (RC) filter 120, and a single operational amplifier 122 (see FIG. 3 in particular). Signal summation circuit sub-block 119 includes resistors R10 and R7 of FIG. 3. RC filter 120 includes a first stage (i.e., capacitor C6 and resistor R9 of FIG. 3) and a second stage (i.e., capacitor C7 and resistor R8 of FIG. 3). In FIG. 3, single operational amplifier 122 is labeled U3.

Clock module 112 and micro-controller 114 are configured to generate a plurality of phase-shifted square wave signals (such as signals A and B depicted in FIG. 4) and output the plurality of phase-shifted square wave signals to signal summation circuit sub-block 119 (see FIG. 3). Signal summation circuit sub-block 119 is configured to sum the plurality of phase-shifted square wave signals to generate a resultant summed-wave signal and output the resultant summed-wave signal to RC filter 120. RC filter 120 is configured to filter harmonics from the resultant summed-wave signal, thereby creating a reduced harmonic distortion signal. Single operational amplifier 122 is configured to amplify the reduced harmonic distortion signal to produce an amplified reduced harmonic distortion signal (e.g., signal C) that is output to an analytical test strip TS received in strip port connector 106.

To illustrate the operation of clock module 112, micro-controller 114 and signal summation circuit sub-block 119, FIG. 5 depicts first and second phase-shifted square waves and the resultant summed-wave signal. In FIG. 5, the uppermost signal is a −30 degree phase-shifted square wave signal while the center signal is a +30 degree phase-shifted square wave signal. The two square wave signals are, therefore, phase-shifted by a total of 60 degrees. The lowermost signal is the resultant summed-wave signal, which is a closer approximation to a sine wave than either of the first or second phase-shifted square wave signals. It has been determined that using two square waves signals that are phase-shifted by 60 degrees to create a resultant summed-wave signal essentially completely eliminates any $3^{rd}$ order harmonics. However, other phase-shifts, such as phase-shifts in the range of 45 degrees to 75 degrees, can also substantially reduce $3^{rd}$ order harmonics.

The effect of phase separation on $1^{st}$ through $5^{th}$ harmonics was studied using the simulation schematic depicted in FIG. 6. The results are shown in FIGS. 7, 8, 9 and 10. In this regard, it is noted that the upper portion of the simulation schematic if FIG. 6 is a $4^{th}$ order filter employing two operational amplifiers while the lower portion is essentially equivalent to the schematic of FIG. 3.

FIGS. 7, 8, 9 and 10 indicate that $1^{st}$ order harmonics are at a maximum for a phase separation of zero degrees and a minimum at a phase separation of 180 degrees. FIG. 8 indicates that $2^{nd}$ and $4^{th}$ order harmonics are minimal due to the input square waves being composed of only odd harmonics. The $3^{rd}$ order harmonic has the largest contribution to Total Harmon Distortion (THD) and has a minimum at phase separations of 60, 180 and 300 degrees (see FIG. 8). The lowest THD is at 60 degrees and 300 degrees (see FIG. 9). FIG. 10 illustrates that the $2^{nd}$, $3^{rd}$ and $4^{th}$ order harmonic THD for low-distortion signal generation circuit block 116 gives similar performance to a $4^{th}$ order RC filter with two operational amplifiers for the circumstance of two square waves shifted by 60 degrees.

In hand-held test meters according to embodiments of the present invention, it has been determined that there is a relationship between the "knee" frequency of an RC filter and a resultant sine wave in that varying the knee frequency varies the attenuation of the $1^{st}$ harmonic and, therefore, controls the amplitude of a resultant sine wave. For example, for a second order RC filter, reducing the amplitude of a generated square wave from 2V peak-to-peak to 20 mV peak-to-peak requires 40 dB of attenuation. This requires the knee frequency to be predetermined at a level one decade (i.e., one order of magnitude) below the desired frequency. Thus, for an exemplary but non-limiting desired frequency of 250 KHz, an RC filter with a knee frequency of 25 kHz is required.

Display 102 can be, for example, a liquid crystal display or a bi-stable display configured to show a screen image. An example of a screen image may include a glucose concentration, a date and time, an error message, and a user interface for instructing an end user how to perform a test.

Strip port connector 106 is configured to operatively interface with an analytical test strip TS, such as an electrochemical-based analytical test strip configured for the determination of hematocrit and/or glucose in a whole blood sample. Therefore, the analytical test strip is configured for operative insertion into strip port connector 106 and to operatively interface with low-distortion signal generation circuit block 116 and phase-shift-based hematocrit measurement block 118 via, for example, suitable electrical contacts.

USB Interface 108 can be any suitable interface known to one skilled in the art. USB Interface 108 is essentially a passive component that is configured to power and provide a data line to hand-held test meter 100.

Once an analytical test strip is interfaced with hand-held test meter 100, or prior thereto, a bodily fluid sample (e.g., a whole blood sample) is introduced into a sample chamber of the analytical test strip. The analytical test strip can include enzymatic reagents that selectively and quantitatively transform an analyte into another predetermined chemical form. For example, the analytical test strip can include an enzymatic reagent with ferricyanide and glucose oxidase so that glucose can be physically transformed into an oxidized form.

Micro-controller 114 also includes a memory sub-block that stores suitable algorithms for the determination of an analyte based on the electrochemical response of analytical test strip and to also determine hematocrit of the introduced sample. Micro-controller 114 is disposed within housing 110 and can include any suitable micro-controller and/or microprocesser known to those of skill in the art. Suitable micro-controllers include, but are not limited to, a micro-controller commercially available from Texas Instruments (Dallas, Tex., USA) as part number MSP430F5636 and a micro-controller commercially available from STMicroelectronics, (Geneva, Switzerland) as part number STM8L152. Micro-controller 114 can, if desired, include a timer block that is employed in the creation of the plurality of phase-shifted square waves.

As described further below, phase-shift-based hematocrit measurement block 118 and micro-controller 114 are configured to measure the phase shift of a bodily fluid sample in a sample cell of an analytical test strip inserted in the hand-held test meter by, for example, measuring the phase shift of one or more high frequency electrical signals driven through the bodily fluid sample. In addition, micro-controller 114 is configured to compute the hematocrit of the bodily fluid based on the measured phase shift.

The amplified reduced harmonic distortion signal produced by low-distortion signal generation circuit block 116 is communicated to strip port connector 106 where it is driven across a sample cell of analytical test strip TS and the resultant signal detected by phase-shift-based hematocrit measurement block 118. Further details regarding the use of sine wave signals for the determination of hematocrit in bodily fluid samples are available in U.S. patent application Ser. No. 13/008,405, which is hereby incorporated in full by reference.

In the embodiment described with respect to FIGS. 1-11, the amplified reduced harmonic distortion signal is a sine wave. However, hand-held test meters according to alternative embodiments of the present invention can be employed to generate other amplified low-distortion signals from a plurality of phase-shifted square wave signals including, for example, an amplified low-distortion trapezoidal wave signal and an amplified low-distortion triangular wave signal. Such trapezoidal and triangular wave signals can be created without the use of a RC filter and the distortion of the amplified signal is reduced as the number of summed phase-shifted square wave signals is increased.

Therefore and in general, alternative embodiments of a hand-held test meter for use with an analytical test strip in the determination of an analyte in, and/or a characteristic of, a bodily fluid sample according to embodiments of the present invention include a housing, a clock module disposed in the housing, a micro-controller disposed in the housing, a low-distortion signal generation circuit block disposed in the housing, and a strip port connector configured to operationally receive an analytical test strip. The low-distortion signal generation circuit block includes a signal summation circuit sub-block and a single operational amplifier.

The clock module and micro-controller are configured to generate a plurality of phase-shifted square wave signals and output the plurality of phase-shifted square wave signals to the signal summation circuit. The signal summation circuit is configured to sum the phase-shifted square wave signals to generate a resultant summed-wave signal and output the resultant summed-wave signal to single operational amplifier. The single operational amplifier is configured to amplify the resultant summed-wave signal to produce a low-distortion amplified signal (such as an amplified low-distortion triangular signal or an amplified low-distortion trapezoidal signal) that is output to an analytical test strip received in the strip port connector.

Figure 11:
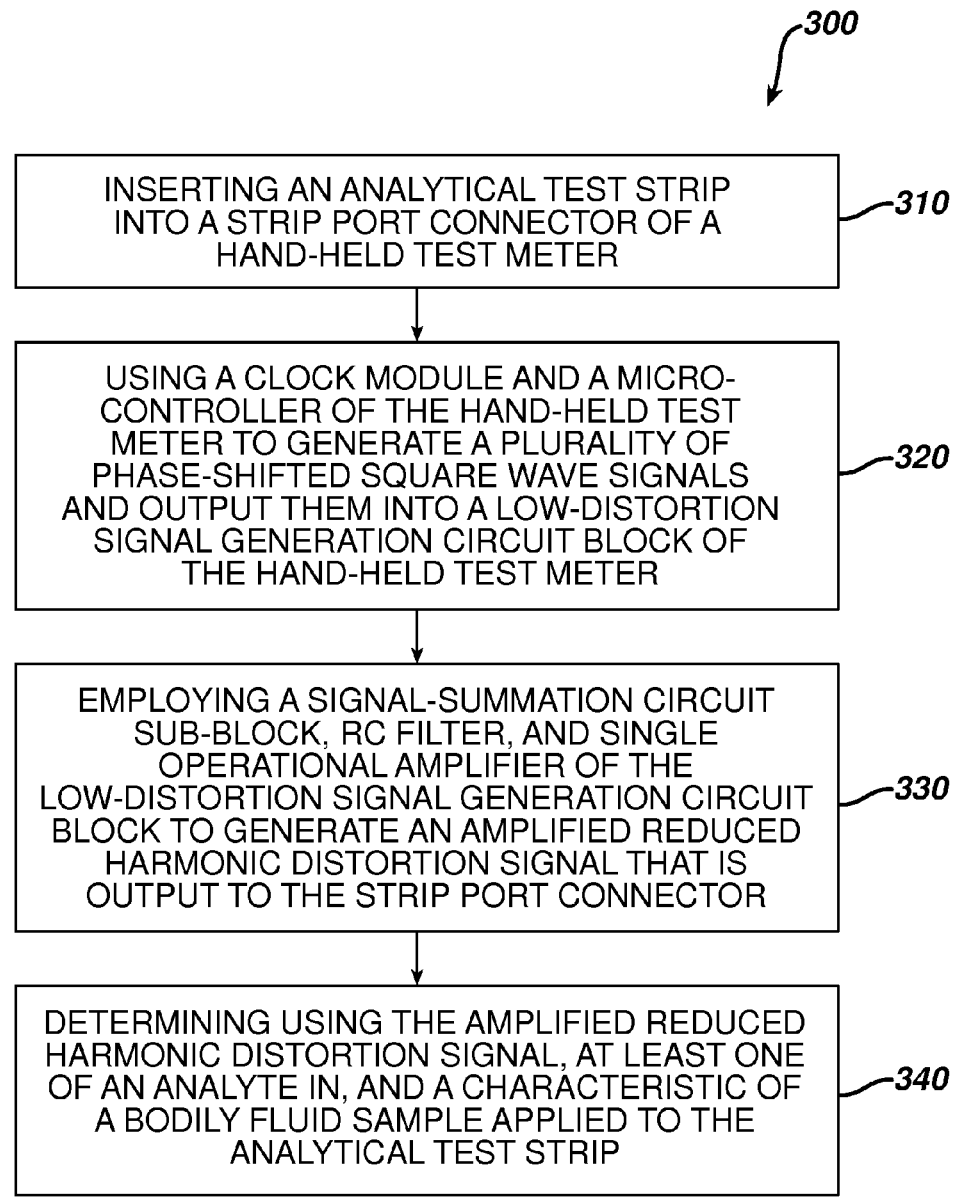
FIG. 11 is a flow diagram depicting stages in a method for employing a hand-held test meter according to an embodiment of the present invention.

FIG. 11 is a flow diagram depicting stages in a method 300 for employing a hand-held test meter (e.g., hand-held test meter 100 of FIG. 1) according to an embodiment of the present invention.

Method 300 includes inserting an analytical test strip into a strip port connector of a hand-held test meter (see step 310 of FIG. 11). The analytical test strip can be any suitable analytical test strip including, for example, an electrochemical-based analytical test strip configured for the determination of glucose and/or hematocrit in a whole blood sample.

At step 320 of method 300, a clock module and a micro-controller of the hand-held test meter are used to generate a plurality of phase-shifted square wave signals and to output the plurality of phase-shifted square wave signals to a low-distortion signal generation circuit block of the hand-held test meter. The plurality of phase-shifted square waves can be phase shifted in a range, for example, between 45 degrees and 75 degrees.

As depicted in step 330 of FIG. 11, a signal summation circuit sub-block, resistance-capacitance (RC) filter and single operational amplifier of the low-distortion signal generation circuit block are employed to (i) sum the plurality of phase-shifted square wave signals to generate a resultant summed-wave signal, (ii) filter harmonics from the resultant summed-wave signal thereby creating a reduced harmonic distortion signal, and (iii) amplify the reduced harmonic distortion signal to produce an amplified reduced harmonic distortion signal that is output to the analytical test strip received in the strip port connector. Alternatively, when an amplified low-distortion triangular or trapezoidal wave signal is to be produced, the RC-filter need not be employed and the resultant summed-wave signal can be amplified to create an amplified low-distortion signal.

In step 340 of method 300, at least one of an analyte in (such as glucose) and a characteristic of (e.g., hematocrit) a bodily fluid sample applied to the analytical test strip is determined using the amplified reduced harmonic distortion signal or, alternatively, an amplified low-distortion signal.

Once apprised of the present disclosure, one skilled in the art will recognize that methods according to embodiments of the present invention, including method 300, can be readily modified to incorporate any of the techniques, benefits and characteristics of hand-held test meters according to embodiments of the present invention and described herein. For example, if desired, an analyte in the introduced bodily fluid sample can be determined using the analytical test strip, hand-held test meter and computed hematocrit.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that devices and methods within the scope of these claims and their equivalents be covered thereby.

What is claimed is:

1. A hand-held test meter for use with an analytical test strip in the determination of an analyte in a bodily fluid sample, the hand-held test meter comprising:
   a housing;
   a clock module disposed in the housing;
   a micro-controller disposed in the housing;
   a low-distortion signal generation circuit disposed in the housing that includes:
      a signal summation circuit;
      a resistance-capacitance (RC) filter; and
      a single operational amplifier; and
   a strip port connector configured to operationally receive an analytical test strip; and
   wherein the clock module and micro-controller are configured to generate a plurality of phase-shifted square wave signals and output the plurality of phase-shifted square wave signals to the signal summation circuit; and
   wherein the signal summation circuit is configured to sum the plurality of phase-shifted square wave signals to generate a resultant summed-wave signal and output the resultant summed-wave signal to the RC filter; and
   wherein the RC filter is configured to filter harmonics from the resultant summed-wave signal thereby creating a reduced harmonic distortion signal; and
   wherein the single operational amplifier is configured to amplify the reduced harmonic distortion signal to produce an amplified reduced harmonic distortion signal that is output to an analytical test strip received in the strip port connector.

2. The hand-held test meter of claim 1 further including a signal phase and magnitude measurement circuit.

3. The hand-held test meter of claim 1 wherein the plurality of phase-shifted square wave signals includes a first phase-shifted square wave signal and a second phase-shifted square wave signal.

4. The hand-held test meter of claim 3 wherein the first phase-shifted square wave signal and the second phase shifted square wave signal have a phase difference in the range of 45 degrees to 75 degrees.

5. The hand-held test meter of claim 4 wherein the first phase-shifted square wave signal and the second phase shifted square wave signal have a phase difference of 60 degrees.

6. The hand-held test meter of claim 1 wherein the microcontroller includes:
   a timer; and
   wherein the timer is employed to create the plurality of phase-shifted square waves.

7. The hand-held test meter of claim 1 wherein the resultant summed wave signal approximates a sine wave signal and is essentially-free of $3^{rd}$ order harmonics.

8. The hand-held test meter of claim 1 wherein the amplified reduced harmonic distortion signal has a total harmonic distortion of less than 1.1%.

9. The hand-held test meter of claim 1 wherein the analytical test strip is an electrochemical-based analytical test strip configured for the determination of glucose and hematocrit of a bodily fluid sample.

10. The hand-held test meter of claim 1 wherein the clock module, micro-controller and low-distortion signal generation circuit are configured to measure the phase shift of a bodily fluid sample in a sample cell of an analytical test strip inserted in the hand-held test meter by forcing amplified low distortion signal of through the bodily fluid sample.

11. The hand-held test meter of claim 1 wherein the amplified reduced harmonic distortion signal is an amplified reduced harmonic distortion sine wave signal.

12. A method for employing a hand-held test meter and analytical test strip, the method comprising:
   inserting an analytical test strip into a strip port connector of a hand-held test meter;
   generating, using a clock module and a micro-controller of the hand-held test meter, a plurality of phase-shifted square wave signals and outputting the plurality of phase-shifted square wave signals to a low-distortion signal generation circuit of the hand-held test meter;
   employing a signal summation circuit, resistance-capacitance (RC) filter and single operational amplifier of the low-distortion signal generation to sum the plurality of phase-shifted square wave signals to generate a resultant summed-wave signal and filter harmonics from the resultant summed-wave signal to thereby create a reduced harmonic distortion signal; and amplify the reduced harmonic distortion signal to produce an amplified reduced harmonic distortion signal that is output to the analytical test strip received in the strip port connector; and determining at least one of an analyte in, and a characteristic of, a bodily fluid sample applied to the analytical test strip using the amplified reduced harmonic distortion signal.

13. The method of claim 12 wherein the employing includes employing the amplified reduced harmonic distortion signal to determine hematocrit of a whole blood sample applied to the analytical test strip.

14. The method of claim 12 wherein the plurality of phase-shifted square waves are a first phase-shifted square wave and a second phase-shifted square wave, a sine wave.

15. The method of claim 14 wherein the amplified reduced harmonic distortion signal is a sine wave.

16. The method of claim 14 wherein the first phase-shifted square wave signal and the second phase shifted square wave signal have a phase difference in the range of 45 degrees to 60 degrees.

17. The method of claim 16 wherein the wherein the first phase-shifted square wave signal and the second phase shifted square wave signal have a phase difference of 60 degrees.

18. The method of claim 12 wherein the first phase-shifted square wave signal and the second phase shifted square wave signal are digital signals.

19. The method of claim 12 wherein the amplified reduced harmonic distortion signal is a sine wave signal.

20. The method of claim 19 wherein the amplified reduced harmonic distortion signal is a sine wave signal with a total harmonic distortion of less than 1.1%.

21. The method of claim 19 wherein the amplified reduced harmonic distortion signal is a sine wave signal essentially free of $3^{rd}$ order harmonics.

22. A hand-held test meter for use with an analytical test strip in the determination of an analyte in a bodily fluid sample, the hand-held test meter comprising:
a housing;
a clock module disposed in the housing;
a micro-controller disposed in the housing;
a low-distortion signal generation circuit disposed in the housing that includes:
a signal summation circuit; and
a single operational amplifier; and
a strip port connector configured to operationally receive an analytical test strip; and wherein the clock module and micro-controller are configured to generate a plurality of phase-shifted square wave signals and output the plurality of phase-shifted square wave signals to the signal summation circuit; and wherein the signal summation circuit is configured to sum the plurality of phase-shifted square wave signals to generate a resultant summed-wave signal and output the resultant summed-wave signal to the single operational amplifier; and wherein the single operational amplifier is configured to amplify the resultant summed wave signal to produce an amplified low-distortion signal that is output to an analytical test strip received in the strip port connector.

23. The hand-held test meter of claim 22 wherein the amplified low-distortion signal is an amplified low-distortion triangular signal.

24. The hand-held test meter of claim 22 wherein the amplified low-distortion signal is an amplified low-distortion trapezoidal signal.

25. A method for employing a hand-held test meter and analytical test strip, the method comprising:
inserting an analytical test strip into a strip port connector of a hand-held test meter;
generating, using a clock module and a micro-controller of the hand-held test meter, a plurality of phase-shifted square wave signals and outputting the plurality of phase-shifted square wave signals to a low-distortion signal generation circuit of the hand-held test meter;
employing a signal summation circuit and single operational amplifier of the low-distortion signal generation to sum the plurality of phase-shifted square wave signals to generate a resultant summed-wave signal and to amplify the resultant summed-wave signal to produce an amplified low-distortion signal that is output to the analytical test strip received in the strip port connector; and
determining at least one of an analyte in, and a characteristic of, a bodily fluid sample applied to the analytical test strip using the amplified low-distortion signal.

26. The method of claim 25 wherein the amplified low-distortion signal is an amplified low-distortion triangular signal.

27. The method of claim 25 wherein the amplified low-distortion signal is an amplified low-distortion trapezoidal signal.

* * * * *